United States Patent [19]
Stockwell

[11] Patent Number: 5,478,332
[45] Date of Patent: Dec. 26, 1995

[54] INTRAVENOUS INJECTION CAP SUPPORT METHOD

[76] Inventor: Trinet Stockwell, 1342 W. Ave., Fullerton, Calif. 92633

[21] Appl. No.: 313,336

[22] Filed: Sep. 27, 1994

[51] Int. Cl.[6] ............................................. A61M 25/00
[52] U.S. Cl. ........................... 604/283; 128/DIG. 26; 604/174
[58] Field of Search .................... 604/283, 174, 604/179; 128/DIG. 26; 248/65, 70

[56] References Cited

U.S. PATENT DOCUMENTS

| | | | |
|---|---|---|---|
| 2,266,230 | 12/1941 | Mazzeo et al. | 128/DIG. 26 |
| 3,210,816 | 10/1965 | Clemons | 128/DIG. 26 |
| 3,702,612 | 11/1972 | Schlessinger | 128/DIG. 26 |
| 4,141,524 | 2/1979 | Corvese, Jr. | 248/70 |
| 4,392,854 | 7/1983 | Ibach | 604/174 |
| 4,955,864 | 9/1990 | Hajduch | 604/174 |
| 5,054,723 | 10/1991 | Arnold | 248/65 |

*Primary Examiner*—John J. Yasko
*Attorney, Agent, or Firm*—Locke Purnell Rain Harrell

[57] ABSTRACT

The apparatus includes a base engaged with a support arm, which support arm is adapted to receive a tubing clip. The tubing clip includes a slot that is adapted to receive intravenous tubing or a central venous catheter and to retain the tubing in a secure manner so as to support in a stationary manner an injection cap associated with the tubing or catheter.

4 Claims, 2 Drawing Sheets

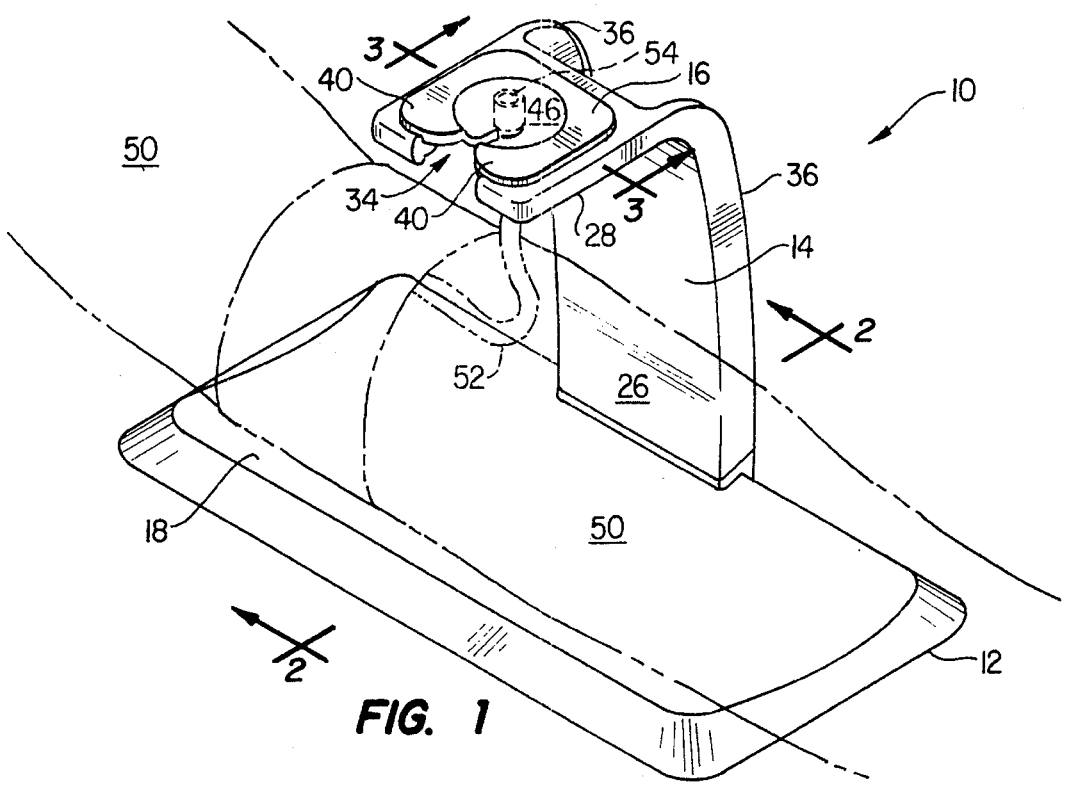
FIG. 1
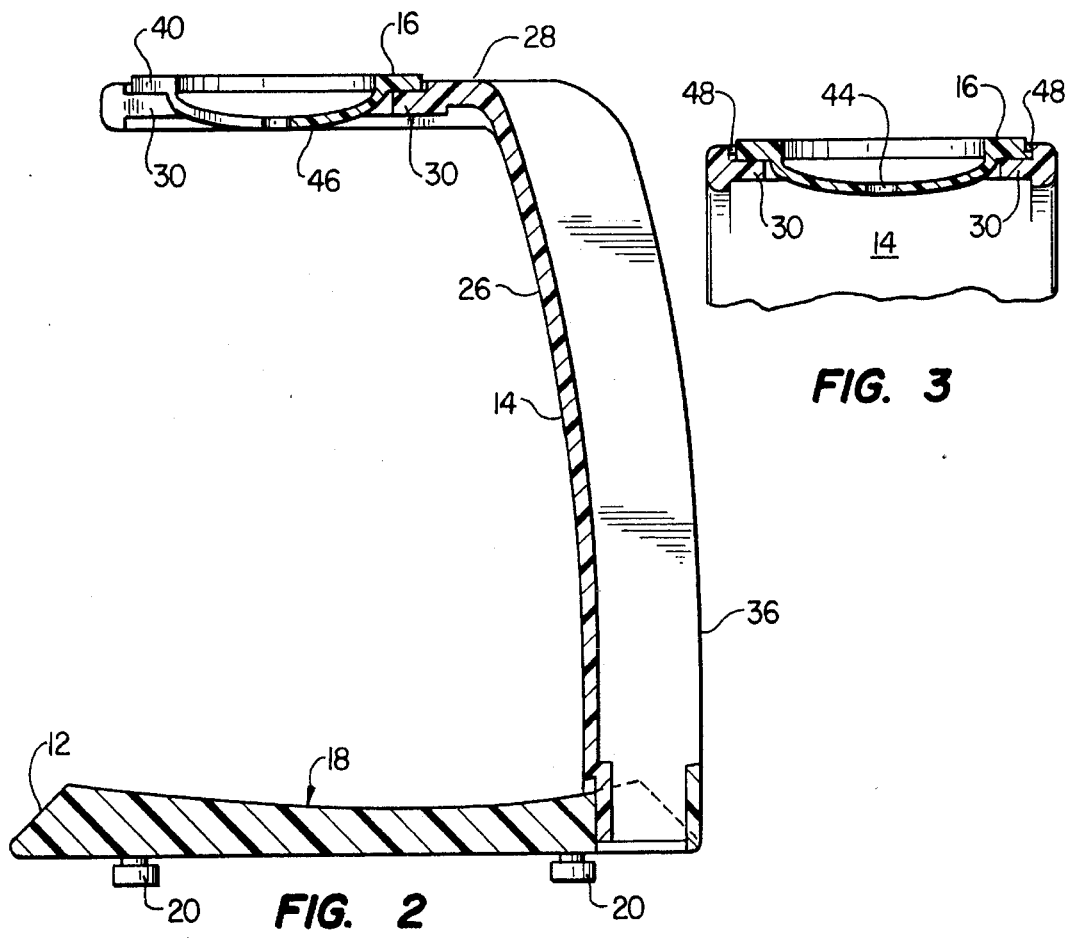
FIG. 2
FIG. 3

INTRAVENOUS INJECTION CAP SUPPORT METHOD

BACKGROUND OF THE INVENTION

1. Field of the Invention

The present invention relates to apparatus for supporting intravenous tubing or a central venous catheter near the point where it connects to an injection cap so the injection cap is held steady. The apparatus finds particular utility in home health care settings.

2. Description of the Prior Art

In an effort to minimize the ever increasing costs of health care, many patients, insurance companies and health maintenance organizations have turned to providing medical care in the patient's home. Often, such home health care programs involve periodic intravenous injections of medicine and other substances. The most efficient means for accomplishing such injections is by administering the substances either through an injection port or cap that is connected by intravenous tubing to an intravenous catheter inserted into the patient's body or through an injection cap that is connected to a central venous catheter inserted into the patient's chest.

An intravenous (IV) delivery system inserted into a medical patient's extremity customarily includes an IV catheter inserted into a vein which is connected by IV tubing to an injection cap. Typically, there is about 4 to 6 inches of IV tubing between the injection cap and the point in a patient's body where the IV tubing is attached to the IV catheter. To administer an IV medication, the injection cap is punctured by a needle attached to a syringe or accessed by another delivery instrument.

An IV delivery system inserted into a medical patient's chest customarily is one of two types. First, there may be an IV catheter inserted into a vein which is connected by IV tubing to an IV injection cap. A second type of system uses a central venous catheter which is inserted into the patient's chest and has a line extending outside the body with an injection cap attached to the end of the line. No IV tubing is required with this second system. To administer an IV medication, the injection cap is punctured by a needle attached to a syringe or accessed by another delivery system.

Since two hands are generally required to perform the injections, it has been quite difficult for a patient to self-administer such injections, especially when the intravenous catheter is inserted into the patient's armor chest. In such instances, many patients require the assistance of another person to administer the medication while the patient holds the injection cap steady. In many cases the other person is a nurse. Obviously, the need for having a nurse present to assist in the administration of intravenous injections increases the patient's health care costs. In view of the objective of minimizing health care costs, it would be advantageous if the patient could self-administer the medication without the need for assistance from another person.

A need exists, therefore, for apparatus for steadying an injection cap connected to intravenous tubing or to a central venous catheter so as to allow a patient to self-inject medication through the injection cap without assistance from another person.

SUMMARY OF THE INVENTION

The apparatus of the present invention overcomes the above-mentioned disadvantages and drawbacks which are characteristic of the prior art.

In a preferred embodiment of the present invention, the apparatus for supporting an intravenous injection cap comprises a base, a support arm engaged with the base and a device for receiving and retaining intravenous tubing or a central venous catheter and an intravenous injection cap that is engaged with the support arm.

The support arm of the apparatus fits into the base of the apparatus and the tubing clip fits into the support arm.

The tubing clip of the apparatus is adapted to separate from the support arm of the apparatus if a patient jerks his arm accidentally. This prevents the patient from pulling the IV catheter out of his arm.

Preferably, the base of the apparatus is concave so that a patient's arm fits comfortably in the apparatus. It is also preferred that the area where the patient's arm fits is smooth while the area outside of where the patient's arm fits may be textured.

It is also preferred that the bottom of the base of the apparatus be as even as possible so that the base of the apparatus is level when placed on a flat, level surface. It is further preferred that the bottom of the base of the apparatus includes rubber feet so that it is stable and does not slip or slide even when a patient with a shaky arm uses the apparatus.

Finally, it is preferred that the base of the apparatus with the rubber feet on it is such that when double sided tape is put on the feet, the base may be securely engaged with an upright mirror.

The IV injection cap support apparatus of the present invention is useful for IV patients in home health care settings. The apparatus also is useful for caregivers and patients in other health care settings such as hospitals, nursing homes, or outpatient clinics. The apparatus holds the patient's injection cap stable and in an upright position so that the patient can see the cap easily and inject the IV medication by himself. Without this device, many patients currently need an extra hand from a household member, friend or nurse to administer the medication. Alternatively, some patients currently attach an additional length of IV tubing, but this is cumbersome and there is a risk that the IV catheter may be pulled out if the extra tubing catches on something.

In addition, the IV injection cap support apparatus of the present invention is designed so that it can be used by patients who have a central line IV inserted into their chest. In this case, the IV injection cap support apparatus is attached to an upright mirror, such as a wall mirror, with double sided tape. The IV tubing or the central venous catheter with the IV injection cap is inserted into the apparatus, and the patient then can look down at the cap and self-administer the IV medication with a syringe into the cap. Such patients with a central IV line may also use the apparatus of the present invention to hold the outer end of the central venous catheter or IV tubing away from their chest so that the site of the catheter insertion may be cleansed more easily and the catheter dressing may be changed more easily.

The base of the IV injection cap support apparatus of the present invention is designed to serve the same purpose as an arm board. An arm board is used to hold the joint straight when an IV catheter is inserted near the wrist or elbow. Thus, those patients who currently require arm boards may choose to just use the apparatus of the present invention.

The apparatus of the present invention is simple and easy to use with one hand. Also, the apparatus preferably is not "handed" and is equally accessible with the patient's left or right hand.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings.

BRIEF DESCRIPTION OF THE DRAWINGS

FIG. 1 is a perspective view of the apparatus for supporting an intravenous injection cap, steadying IV tubing or steadying a central venous catheter according to the present invention;

FIG. 2 is a cross section view taken along line 2—2 of FIG. 1;

FIG. 3 is a cross section view taken along line 3—3 of FIG. 1; and

DESCRIPTION OF THE PREFERRED EMBODIMENTS

Figure 4:
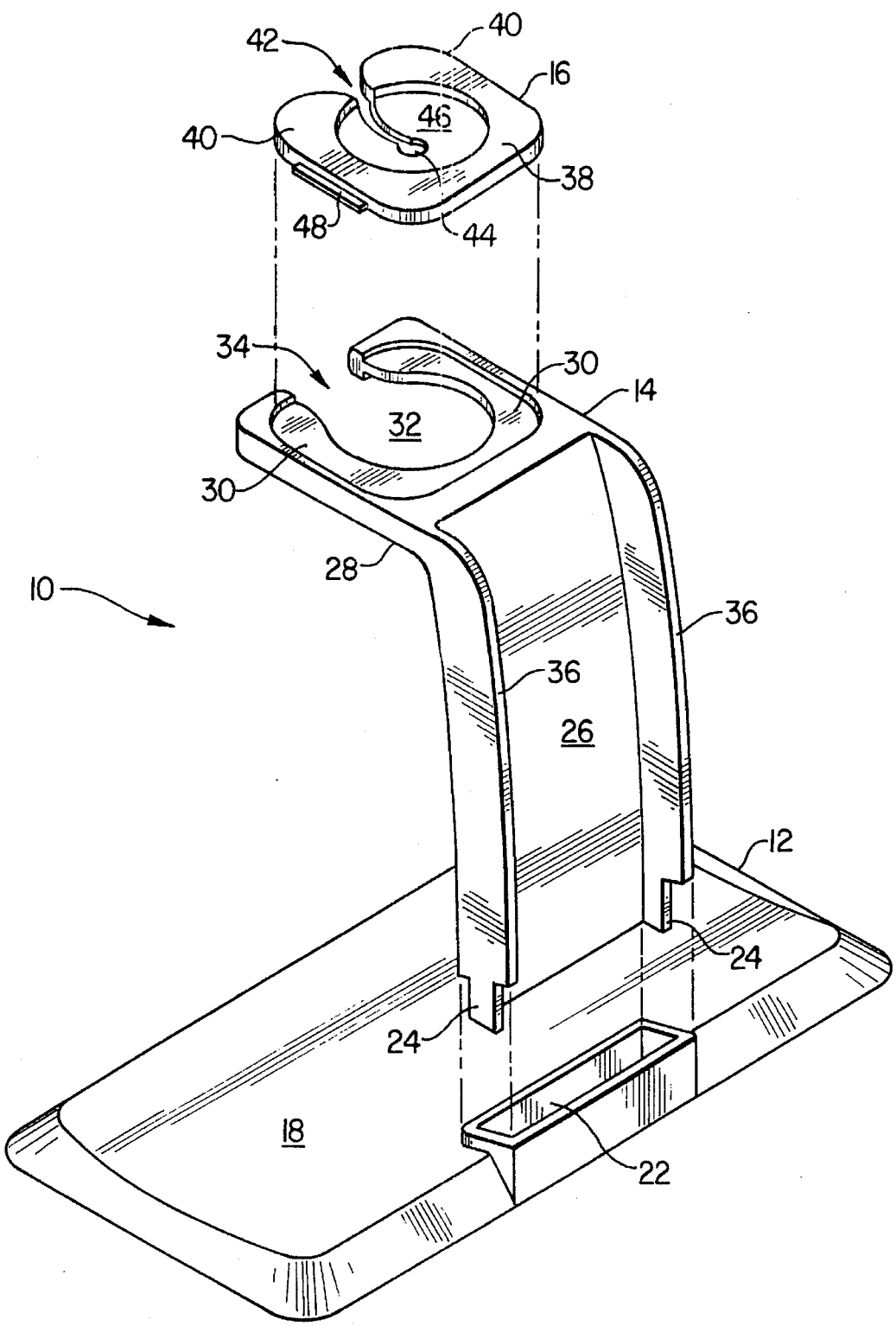
FIG. 4 is an exploded view of the apparatus shown in FIG. 1.

Referring now to the drawings, and particularly to FIG. 1, the apparatus for supporting an intravenous injection cap, steadying IV tubing or steadying a central venous catheter of the present invention is shown and generally designated by the reference numeral 10. For purposes of this application, the term "infusion therapy tubing" is defined to mean and include intravenous tubing and central venous catheters. Preferably, the infusion therapy tubing has a female end to which an intravenous injection cap can be attached and through which medication can be dispensed. As shown in FIG. 1, the support apparatus 10 includes a base 12, a support arm 14 and a tubing clip 16.

The base 12 of the apparatus 10 has a generally rectangular shape with an upper surface 18 as shown in FIG. 2. Preferably, the upper surface 18 has a slight concave curve about the long axis of the base 12 so that the base 12 can be used in place of an arm board.

A plurality of feet 20 is disposed on the bottom of the base 12 opposite the upper surface 18. Preferably, the base 12 includes four feet 20. In another preferred embodiment of the present invention, the feet 20 comprise a non-skid material such as rubber inserts so that the apparatus 10 will not easily slip or slide when placed upon a flat, level surface.

As shown in FIG. 4, the base 12 includes a socket 22 that is adapted to provide an interference fit with a post of the support arm 14 described below.

In a preferred embodiment, the bottom of base 12 opposite the upper surface 18 is substantially hollowed out but includes a rib structure for providing strength and stability to the base 12.

In another preferred embodiment, the base 12 comprises a high impact ABS thermoplastic material and the base 12 is formed by injection molding techniques well known to those of ordinary skill in the art. It will be understood by those of ordinary skill in the art that "ABS" refers to a family of thermoplastic materials that contain three monomeric building blocks—acrylonitrite, butadiene, and styrene. Suitable ABS thermoplastic materials for utility in the apparatus of the present invention are well known in the art.

The support arm 14 of the apparatus 10 includes a post 24 that is adapted to provide an interference fit with the socket 22 of the base 12 so as to engage the support arm 14 with the base 12.

The support arm 14 also includes a generally vertically extending portion 26 and a generally horizontally extending portion 28. As shown in FIG. 1, when the support arm 14 is engaged with the base 12 in the manner described above, the generally vertically extending portion 26 of the support arm 14 extends perpendicular to the upper surface 18 of the base 12 and the generally horizontally extending portion 28 of the support arm 14 is disposed over and extends parallel to the upper surface 18 of the base 12.

Preferably, the generally horizontally extending portion 28 of the support arm 14 includes a recessed portion 30 as shown in FIG. 2. The recessed portion 30 is adapted to provide an interference fit with the edges of the tube clip 16. As shown in FIG. 4, the horizontally extending portion 28 is a generally C-shaped member having an aperture 32 with an opening 34 which is disposed opposite the vertically extending portion 26 of the support arm 14.

In a preferred embodiment, the vertically extending portion 26 of support arm 14 includes a pair of flanges 36 for providing support and stability to the support arm 14 and for preventing twisting of the support arm 14 about its vertical axis.

In another preferred embodiment of the present invention, the support arm 14 comprises a high impact ABS thermoplastic material and the support arm 14 is formed by injection molding techniques well known to those of ordinary skill in the art.

As shown in FIG. 4, the tubing clip 16 of the apparatus 10 is a generally C-shaped member with a body 38 and a pair of arms 40 that extend in a generally parallel manner. A slot 42 extends between the arms 40. The slot has a substantially cylindrical terminus 44. The width of the slot 42 and the diameter of the cylindrical terminus are adapted to provide an interference fit with the uppermost portion of the infusion therapy tubing near the point where it connects to the injection cap.

It is also preferred that the tubing clip includes a recessed portion 46 and that the tubing clip 16 includes projections to provide an interference fit with the recessed portion 30 of the support arm 14.

In another preferred embodiment of the present invention, the tubing clip 16 comprises a high impact ABS thermoplastic material and the tubing clip 16 is formed by injection molding techniques well known to those of ordinary skill in the art.

When it is desired to utilize the apparatus 10, the post 24 of the support arm 14 is inserted within the socket 22 of the base 12. Next, the tubing clip 16 is inserted into the recessed portion 30 of support arm 14.

As shown in phantom in FIG. 1, when used by a patient having an IV catheter (not shown) inserted in his arm 50, the apparatus 10 of the present invention is placed on a flat surface such as a table (not shown). The patient then places his arm 50 in which the IV catheter is placed on the upper surface 18 of the base 12 of the apparatus 10. Those of ordinary skill in the art will recognize that the base 12 could be modified to include straps which include Velcro® or other similar means so as to more securely hold the patient's arm to the base 12.

The patient then uses his hand on the arm that does not have the IV catheter inserted in it to grasp the IV tubing 52 approximately 2 to 3 inches below the injection cap 54 and to slide the tubing 52 into the slot 42 of the tubing clip 16 until the tubing 52 is disposed in the cylindrical terminus 44.

Using the same hand, the patient then reaches under the tubing clip 16 and gently pulls the IV tubing 52 downward until it fits snugly in the cylindrical terminus 44.

Now that the tubing 52 is held firmly, the patient may then perform a procedure according to instructions given by the patient's doctor or nurse. The types of procedures patients may be performing include, but are not limited to, puncturing the injection cap 54 with a needle attached to a syringe (not shown) to inject a medication, attaching a syringe directly to the injection cap to inject a medication according to a needleless system, attaching IV tubing, or changing the injection cap.

Upon completion of a procedure, the patient may remove the IV tubing 52 from the apparatus 10 by simply grasping the cap 54 and pulling it upward with respect to the tubing clip 16. The tubing clip 16 of the apparatus 10 may release from the support arm 14 with the tubing 52, but the tubing clip 16 can be removed from the tubing 52 and fitted back into the arm 14 of the apparatus 10.

When the apparatus 10 is to be used by patients who have a central line IV inserted into their chest, the apparatus 10 is assembled in the same manner as described above. The patient then finds an upright mirror that he or she can sit or stand comfortably 1 to 2 feet in front of while using the apparatus 10. Next, the patient may attach double sided tape to the feet 20 on the bottom of the base 12 of the apparatus 10 and position the apparatus 10 on the mirror so that the long axis of the base 12 extends in a vertical manner and the slot 42 in the tubing clip 16 is disposed on the side of the apparatus 10 that is most convenient for the patient.

The patient then grasps the infusion therapy tubing approximately 2 to 3 inches below the injection cap and slides it into the slot 42 of the tubing clip 16 in a direction away from the patient's body until the infusion therapy tubing is disposed in the cylindrical terminus 44.

The patient then reaches under the tubing clip 16 and gently pulls the infusion therapy tubing until it is held snugly in the cylindrical terminus 44.

The patient may then perform a procedure according to instructions given by the patient's doctor or nurse. The types of procedures patients may be performing include, but are not limited to, puncturing the injection cap with a needle attached to a syringe to administer a medication, attaching a syringe directly to the injection cap to inject a medication according to a needleless system, attaching IV tubing, or changing the injection cap.

The patient may also use the apparatus 10 to hold the outer end of the infusion therapy tubing away from the patient's chest so as to change the catheter dressing more easily.

Upon completion of a procedure, the patient may remove the infusion therapy tubing from the apparatus 10 by simply grasping the cap and pulling it in a direction away from the tubing clip 16 and the base 12. The tubing clip 16 of the apparatus 10 may release from the support arm 14 with the infusion therapy tubing, but the tubing clip 16 can be removed from the infusion therapy tubing and fitted back into the support arm 14 of the apparatus 10.

It is preferred that the apparatus be durable enough to be used 80–100 times, although it may be used only about 25 times and replaced weekly for the sake of cleanliness. With average use the useful life of the apparatus preferably is about 1 to 4 weeks.

The distance between the base and the top of the apparatus preferably is sufficient, such as 5 to 6 inches, so as to clear a large man's (200 to 250 lbs.) arm by 1 inch.

It is preferred that the top of the apparatus holds the infusion therapy tubing approximately $\frac{1}{8}$ inch below the area where the bottom of the injection cap and the infusion therapy tubing are connected.

The infusion therapy tubing preferably is held tightly so that a syringe can be connected to the injection cap or the injection cap can be removed with one hand.

The three-piece design of the preferred apparatus facilitates the packing thereof.

It is preferred that the apparatus be useful with all currently used sizes of IV caps and infusion therapy tubing.

While preferred embodiments of the invention have been shown and described, it will be understood by persons skilled in the art that various changes and modifications may be made therein without departing from the spirit and scope of the invention which is defined by the following claims.

What is claimed is:

1. A method for securing infusion therapy tubing, comprising the steps of:
   a) engaging infusion therapy tubing connected to an intravenous injection cap adjacent said connection of said infusion therapy tubing and said intravenous injection cap with apparatus for securing infusion therapy tubing, which apparatus comprises:
      1) means for supporting said apparatus on a surface; and
      2) means for attaching said apparatus to said infusion therapy tubing, and said attaching means being engaged with said supporting means and being adapted to disengage from said support means upon movement of said infusion therapy tubing in a direction away from said supporting means.

2. A method according to claim 1, wherein said apparatus is placed on a flat, level surface.

3. A method according to claim 1, wherein said infusion therapy tubing is inserted in a patient's arm and wherein said patient places said arm on said supporting means of said apparatus.

4. A method according to claim 1, wherein said infusion therapy tubing is secured whereby said patient injects an intravenous solution by puncturing said intravenous injection cap with a needle attached to a syringe, injects an intravenous solution by attaching a syringe directly to said injection cap, attaches additional infusion therapy tubing to said infusion therapy tubing or changes said injection cap.

* * * * *

UNITED STATES PATENT AND TRADEMARK OFFICE
CERTIFICATE OF CORRECTION

PATENT NO.  : 5,478,332
DATED       : December 26, 1995
INVENTOR(S) : Trinet Stockwell It is certified that error appears in the above-indentified patent and that said Letters Patent is hereby corrected as shown below:

Column 1, line 47, change "armor" to -- arm or --.

Signed and Sealed this

Second Day of April, 1996

Attest:

BRUCE LEHMAN

Attesting Officer

Commissioner of Patents and Trademarks